United States Patent
Juarez Molina et al.

(10) Patent No.: US 11,896,013 B2
(45) Date of Patent: Feb. 13, 2024

(54) ***DOMINIKIA* SP. STRAIN, COMPOSITIONS COMPRISING IT AND USES**

(71) Applicant: SYMBORG, SL, Murcia (ES)

(72) Inventors: Jesus Juarez Molina, Murcia (ES); Felix Fernandez, Murcia (ES); Antonio Jose Bernabe Garcia, Murcia (ES); Ana Vila Martinez, Cartagena (ES); Rocio Torres Vera, Granada (ES)

(73) Assignee: SYMBORG, SL, Murcia (ES)

( * ) Notice: Subject to any disclaimer, the term of this patent is extended or adjusted under 35 U.S.C. 154(b) by 518 days.

(21) Appl. No.: 17/273,808

(22) PCT Filed: Sep. 11, 2019

(86) PCT No.: PCT/IB2019/057647
§ 371 (c)(1),
(2) Date: Mar. 5, 2021

(87) PCT Pub. No.: WO2020/053780
PCT Pub. Date: Mar. 19, 2020

(65) Prior Publication Data
US 2021/0307334 A1    Oct. 7, 2021

(30) Foreign Application Priority Data
Sep. 12, 2018  (EP) .................... 18382653

(51) Int. Cl.
*A01N 25/00* (2006.01)
*A01N 25/12* (2006.01)
*A01N 63/30* (2020.01)
*A01P 5/00* (2006.01)
*A01P 21/00* (2006.01)
*C12N 1/14* (2006.01)

(52) U.S. Cl.
CPC ............. *A01N 63/30* (2020.01); *A01N 25/12* (2013.01); *C12N 1/145* (2021.05)

(58) Field of Classification Search
None
See application file for complete search history.

(56) References Cited

FOREIGN PATENT DOCUMENTS

WO    2015000612 A1    1/2015
WO    2015000613 A1    1/2015

OTHER PUBLICATIONS

F. Fernandez Martin, et al; Application of arbuscular mycorrhizae *Glomus iranicum* var. *Tenuihypharum* var. nova in intensive agriculture: a study case; Journal of Agricultural Science and Technology B; vol. 7; No. 4; Apr. 28, 2017; XP055520245; pp. 221-247 (English).
F. Fernandez, et al; Physiological and growth responses of young tomato seedlings to drip-irrigation containing two low doses of the arbuscular mycorrhizal fungus *Glomus iranicum* var. *Tenuihypharum* sp. nova; Journal of Horticultural Science and Biotechnology; vol. 89; No. 6; Jan. 1, 2014; XP055520249; pp. 679-685 (English).
E. Nicolas, et al; Inoculacion y persistencia del hongo micorrizico arbuscular *Glomus iranicum* var. tenuihypharum; Agricultura; Oct. 1, 2013; XP055520253; pp. 674-678 (Spanish only).
International Search Report and Written Opinion for PCT/IB2019/057647 dated Oct. 23, 2019; 8 pages in English.

*Primary Examiner* — Alton N Pryor
(74) *Attorney, Agent, or Firm* — LUCAS & MERCANTI, LLP

(57) ABSTRACT

The strain of fungus *Dominikia* sp. deposited under accession number MUCL 57072, that can be included into compositions is disclosed; the composition being suitable to be used as bio-stimulant and bio-nematicidal in plants, preferably in cereals. Also disclosed is a process for obtaining said compositions.

13 Claims, 3 Drawing Sheets

DOMINIKIA SP. STRAIN, COMPOSITIONS COMPRISING IT AND USES

CROSS REFERENCE TO RELATED APPLICATION

This Application is a 371 of PCT/162019/057647 filed on Sep. 11, 2019, which claims priority of European Patent Application No. 18382653.6 filed Sep. 12, 2018, both of which are incorporated herein by reference.

FIELD OF THE INVENTION

The present invention relates to the agronomic field. Specifically, it relates to a *Dominikia* sp. strain, compositions comprising it and uses of said compositions, such as the use as bio-stimulant and bio-nematicidal. Compositions comprising a *Dominikia* sp. strain were found to be particularly useful in cereal crops.

BACKGROUND ART

Currently approximately 300 species in 30 genera are described in the Glomeromycota. However, nucleic acid (DNA, RNA) based biodiversity studies point towards a much higher diversity in Glomeromycota and several new species and genera have been described recently.

Most Glomeromycota are arbuscular mycorrhizal fungi (AMF) which are mutualistic symbionts of approximately 80% of all vascular land plants. Nutrient uptake of plants which are colonised by AMF occurs directly via the root epidermis and the root hairs, but also via the fungus-root-interface which has the characteristic form of arbuscules or intraradical hyphal coils. Besides their role in enhancing nutrient uptake in their host, AMF play important roles in soil aggregation and in protecting plants against drought stress and soil born plant pathogens. Because of this highly beneficial nature, several mycorrhizal compositions are known in the art, and they have been developed to provide beneficial effects on the crops they are provided to.

WO2015/000612 and WO2015/000613 disclose compositions comprising *Glomus iranicum* var. *tenuihypharum* var. nov. strain and their uses.

In particular, WO2015/000612 discloses a composition comprising *Glomus iranicum* var. *tenuihypharum* var. nov. strain and 2:1 smectite clays. The composition of WO2015/000612 is disclosed to provide a positive impact on crop yield, i.e. that can be used as bio-stimulant, in lettuce crops.

Similarly, WO2015/000613 discloses a composition comprising *Glomus iranicum* var. *tenuihypharum* var. nov. strain and 2:1 smectite clays, metal ions and chitin. WO2015/000613 discloses that said composition acts as bio-nematicidal in tomato crops.

However, the compositions disclosed in the prior art do not provide an acceptable positive impact on cereal crops, both in terms of bio-stimulant and bio-nematicidal effect.

SUMMARY OF THE INVENTION

An aim of the present invention is thus to provide a strain of fungus that is suitable to be included into compositions, namely compositions suitable to provide a positive impact on crops, in particular on cereal crops.

Another aim of the invention is to provide a composition that is effective as bio-stimulant on cereal crops.

Still another aim of the present invention is to provide a composition that is effective as bio-nematicidal on cereal crops.

A further aim of the present invention is to provide a process to for obtaining compositions.

DETAILED DESCRIPTION

An object of the present invention is thus a strain of Glomeromycota, i.e. a *Dominikia* sp. strain, deposited under accession number MUCL 57072.

The strain of the invention was isolated from a very hydromorphic, highly compacted sodium saline soil type (Solonetz Gley) with a lot of salt deposit at the surface, in the locality of Fortuna, Murcia (Spain).

*Dominikia* sp. strain of the invention was deposited on 21 Mar. 2018 at the International Depositary Authority Belgian Coordinated Collections of Micro-organisms (BCCM), Université catholique de Louvain, Mycothequèque de l'Université catholique de Louvain (MUCL), Croix du Sud 2, box L7.05.06, 1348 Louvain-la-Neuve, Belgium, by Symborg S. L., with address Campus de Espinardo, 7, edificio CEEIM, 30100 Murcia, Spain.

The strain *Dominikia* sp. of the invention has been identified by the depositor with the reference SMB01, and received the deposit number MUCL 57072 by the international depositary authority.

The deposit was made under the terms of the Budapest Treaty. All restrictions upon public access to the deposit will be irrevocably removed upon the grant of a patent on this application. The deposit will be replaced by Applicant if viable samples cannot be dispensed by the depository.

The Sporocarps of the strain of the invention are unknown. In the strain of the invention, spores occurs in loose clusters in the soil, and may be terminal or intercalary; spores may be also formed within the roots. Spores are hyaline to light ochraceous, with a subglobose to globose structure (rarely irregularly), relatively small, i.e. from 24.0 to 42 µm in diameter, with an average value of 30.7±3.7 µm in diameter. Spores present a composite three-layered spore wall (1-4 µm thick). Particularly, an outer layer, a middle layer and an inner layer can be recognized.

The outer layer of the spore wall is substantially mucilagous and evanescent, thus giving young spores a rough appearance, while older spores show a somewhat shaggy appearance. The outer layer of the spore wall exhibits a dextrinoid reaction, when stained with Melzer's reagent, giving young spores a brownish red color. The middle layer of the spore wall is substantially permanent, and is 0.5-2.0 µm thick.

The inner layer of the spore wall is substantially laminar, with a thickness of 0.5-1.5 µm. The contents of the spores have a pale and guttulate appearance. The hyphae that hold the spores have a hyaline to pale ochraceous color, and are straight or wavy of 2.5-4.5 µm in diameter (with an average value of 3.0 µm) The hyphae have a cylindrical to slightly funnel shape, which merges with the open-pored layers of the spore wall, at least in mature spores. The germination structure comprises a germ tube grown and develops back through the union of the hyphae with the spores. It forms vesicular arbuscular mycorrhizae.

The extraradical mycelium forms an extensive network.

A phylogenetic analysis of 134 18S rDNA sequences, including environmental and referenced sequences, was generated by the Applicant. From most *Dominikia* species no or relatively short partial 18S sequences are available. *Dominikia* indica and *D. iranica* sequences can be included in this phylogenetic analysis. The sequences of these two species were shorter than those of the rest of the dataset. Trimming the dataset to the length of these sequences resulted in rather incompletely resolved trees. Using the full length sequences, trees with branches representing the higher taxonomic levels could be generated. However, a robust, monophyletic Glade consisting of sequences from *Dominikia* spp. could not be generated with this dataset. *Dominikia* sp. forms one, well supported Glade together with *Dominikia iranica* and anonymous, environmental glomeralean sequences from different host plants and different locations.

Phylogenetic analysis of an SSU-ITS1 dataset including sequences from the majority of described *Dominikia* species indicates that *Dominikia* sp. branches next to *D. aurea*.

Small spores (up to 65-70 μm of diameter), usually aggregated in loose to compact clusters, are characteristic for the genus *Dominikia*. The spore wall of the members of the genus *Dominikia* consists of two or three layers. The outer layer, forming the spore surface, is mucilaginous, short-lived and stains in Melzer's reagent or is unit (not divided into sublayers), permanent and does not react in Melzer's reagent. The hyphae which hold the spores are cylindrical to funnel-shaped with a pore that may be open or occluded by a septum. *Dominikia minuta* (Basidionym: *Glomus minutum*) was designated as type-species. The strain of the invention, i.e. *Dominikia* sp., has hyaline spores of substantially the same size than those of *Dominikia minuta* but, in contrast to *Dominikia* sp., the pore of. *G. minutum* (i.e. *Dominikia minuta*) is occluded by a septum. D. sp. also differs from *Dominikia minuta* by its three-layers spore wall, as opposed to the two-layered spore wall in *D. minuta*, and because of the presence of the dextrinoid reaction, which is absent in *Dominikia minuta*.

*Dominikia* sp. also differs from the other described *Dominikia* species and strains. The outer layer and the inner layer of spores of *Dominikia* achra stain deeply red in Melzer's reagent, while in *Dominikia* sp. only the outer layer shows a dextrinoid reaction. *Dominikia* indica differs from *Dominikia* sp. by forming small, hyaline spores in hypogeous aggregates. The spore wall of *D. indica* consists of two hyaline layers: a mucilaginous, short-lived, thin outer layer staining pinkish to pink in Melzer's reagent and a laminate, smooth, permanent, thicker inner layer as opposed to the three layers in *Dominikia* sp.

Based on the 18S-ITS1 phylogeny, *Dominikia aurea* is the closest relative of the *Dominikia* sp. strain of the invention. The two species differ in many morphologically characters (see Table 1), the most evident difference being the mostly ovoid spores of *Dominikia aurea* which are aggregated in irregular sporocarps.

TABLE 1

| | *Dominikia aurea* (Oehl et al. 2003) | *Dominikia* sp. |
|---|---|---|
| spore aggregation | irregular sporocarps without peridium | loose clusters |
| intraradical spores | Not described | present |
| intercalary spores | Not described | present |
| colour | Light orange to orange | ochraceous |
| form | Ovoid, rarely globose | globose to subglobose |
| size | Ovoid spores: (36-)55-65 × (30)45-52 μm Globose spores: (27-)40-60 μm | (24.0) 30.7 ± 3.7 (42) μm |

TABLE 1-continued

| | *Dominikia aurea* (Oehl et al. 2003) | *Dominikia* sp. |
|---|---|---|
| spore wall Outermost layer | two layered evanescent, hyaline up to 1.5 μm, deteriorated in mature spores, dextrinoid | three layered mucilaginous, roughened, hyaline (0.4-) 1.0 (1.5) μm, deteriorated in mature spores, dextrinoid |
| Middle layer | | permanent, slightly rough 0.5-2.0 μm thick |
| Innermost layer | laminate, light orange, 1.5-3 (-4) μm | laminate, smooth (0.5-1.5 μm) |
| Subtending hypae | Light orange to orange, straight or curved, cylindrical or slightly funnel shaped; 6-10 μm | hyaline to pale ochraceous, straight or undulating 2.5-5 μm |
| Germination | Unknown | Through the subtending hypha |

Many highly similar sequences to the *Dominikia* sp. of the invention sequences could be found when blasted against gene bank (e-value 0.00, Identity 99%). These sequences occur from wide range of different hosts (e.g. liverworts, monocotyledons) from different countries and continents, indicating a world-wide distribution. These findings indicate that *Dominikia* sp. is widely distributed.

As above mentioned, *Dominikia* sp. was found to be particularly useful to be included into compositions, in particular compositions to be provided to cereal crops.

Another object of the invention is a composition comprising *Dominikia* sp., deposited on 21 Mar. 2018 under accession number MUCL 57072, as above mentioned.

Without being bound to a specific explanation, it has been surprisingly observed that *Dominikia* sp., and composition comprising the same, are particularly effective in providing beneficial effects to crops, in particular to cereal crops.

In particular, it has been observed that, by providing a composition comprising *Dominikia* sp. to a crop, e.g. to a cereal crop (for example, a maize crop, a wheat crop, a barley crop, or a rice crop) an increase in the uptake of the nutrient and an improvement in the yield of the cereal crop can be obtained, with respect to crops that were not provided with *Dominikia* sp. Preferably, the concentration of the *Dominikia* sp. in the composition is from 4.0% to 1.0% by weight, more preferably from 3.0% to 2.0% by weight, even more preferably 2.5% to 2.3% by weight.

According to embodiments, the composition of the invention, is a liquid, a solid or a gel composition.

Preferably, the composition of the invention, is a solid composition.

According to embodiments, the composition of the invention may be in the form of powder, emulsifiable concentrate, granules, or microgranules.

The composition of the invention is a solid composition, and the concentration of the propagules of *Dominikia* sp. in the composition, is measured according to the "Most Probable Number Method" (Porter, Aust. J. Soil Res., 1979, 17, 515-19) from 180 to 120 propagules per gram of composition, preferably from 150 to 120 propagules per gram of composition, more preferably from 125 to 120 propagules per gram of composition.

The concentration of the propagules is referred to the concentration of the propagules in the final product.

According to a preferred embodiment, the composition of the invention is in the form of microgranules.

According to embodiments, said microgranules have a size ranging from 500 µm to 2000 µm, preferably from 800 µm to 1500 µm, more preferably from 900 µm to 1200 µm.

Advantageously, the concentration of the *Dominikia* sp. in the composition of the invention, as well as the form of presentation of the composition, e.g. microgranules, may be selected according to the predetermined final application.

According to embodiments, the composition of the invention further comprises at least one fungicide and/or at least one bio-fungicide and/or at least one insecticide and/or at least one bio-insecticide and/or at least one nematicide and/or at least one bio-stimulant.

According to a preferred embodiment, the composition of the invention is in the form for seeds coating.

For example, said fungicide is selected from the group consisting of Maneb, Mancozeb, Metalaxyl-Ridomil, Myclobutanil, Olpisan, Propamocarb, Quintozene, Streptomycin, Sulfur, Thiophanate-methyl, Thiram, triforine, vinclozolin, Zinc white, Zineb, Ziram, Banrot, Fixed copper, Chlorothalonil, Chlorothalonil, Captan, Chloroneb, Cyproconazole, Zinc ethelene, bisdithiocarbamate, Etridiazole, Fenaminosulf, Fenarimol, Flutolanil, Folpet, Fosetyl-AL and Iprodione.

Exemplary bio-fungicides are: *Trichodermas* sp, *Bacillus subtilis, Bacillus licheniformis, Bacillus pumilus, Bacillus amyloliquefaciens, Streptomyces* sp, *Coniothyrium minitans* and *Pythium oligandrum.*

According to embodiments, the insecticide is selected from the group consisting of organophosphate, carbamate and neonicotinoid.

According to embodiments, said bio-insecticide is selected from the group consisting of *Bacillus* sp., *Chromobacterium* sp., *Beauveria* sp. and *Metarhizium* sp.

According to embodiments, said nematicide is organophosphate or carbamate.

According to embodiments, said bio-nematicide is Pasteuria sp.

Another object of the present invention is a process for the production of a composition comprising the *Dominikia* sp. strain of the invention.

The process of the invention comprises the following steps:

a. Providing a substrate;
b. Providing said substrate with the seeds of a host plant and with *Dominikia* sp. strain deposited under accession number MUCL 57072;
c. Cultivating said host plant and watering to maintain said substrate with a moisture level of at least 75% of field capacity;
d. Discontinuing said watering for a period of at least 7 days;
e. Removing the aerial part of said host plant and the substrate;
f. Drying the removed substrate;
g. Milling the dried substrate to obtain granules having a particle size of below 100 μm.

Preferably, the substrate comprises a clay.

According to embodiments, the *Dominikia* sp. provided in step b. is an inoculum comprising *Dominikia* sp. propagules. Preferably, said inoculum is obtained by providing the root system of a host plant with a substantially pure *Dominikia* sp., cultivating said host plant on a substrate preferably comprising a clay (preferably a sterile smectite clay), preferably for a life cycle of the host plant, and subsequently extracting the root system, to obtain an inoculum. In this case, the inoculum comprises an amount of the substrate, rootlets, and *Dominikia* sp. propagules.

According to a preferred embodiment, the process of the invention further comprises a step h1. of microgranulation.

Preferably, by microgranulation, a composition comprising the *Dominikia* sp. strain of the invention in the form of microgranules may be obtained.

As above mentioned, said microgranules have a size ranging from 500 μm to 2000 μm, preferably from 800 μm to 1500 μm, more preferably from 900 μm to 1200 μm.

According to a preferred embodiment, the process of the invention further comprises a step h2. of preparation of a concentrate biological inoculant for seeds coating of cereals, namely concentrate biological inoculant for seeds coating of cereals of the milled product obtained according to step g. It has to be noted that, in this context, the step h2. of concentrate biological inoculant for seeds coating of cereals is meant as a step wherein the concentration of the *Dominikia* sp. (e.g., the *Dominikia* sp. propagules) in the composition increases.

For example, said step h2. of concentration may be carried out by sieving the milled product obtained according to step g. to select the granules having a particle size above a predetermined value, e.g., above 35 μm.

Advantageously, the concentration step h2. allows to increase the concentration of *Dominikia* sp. (e.g., the *Dominikia* sp. propagules) up to 10 times the initial concentration, preferably up to 50 times the initial concentration (i.e. the concentration of *Dominikia* sp. in the product before step h2), more preferably up to 100 times the initial concentration, i.e. 100 times with respect to the concentration of the composition before step h2. According to embodiments, it is possible to increase the concentration of *Dominikia* sp. (e.g., the *Dominikia* sp. propagules) more than 100 times the initial concentration (i.e. the concentration of *Dominikia* sp. in the product before step h2).

According to a preferred embodiment, the process of the invention further comprises a step i. of seeds coating, namely seeds coating of the concentrate product obtained according to step h2.

Said step i. of seed coating comprises the following steps:

i1. Covering the seeds are with an adhesive substance
i2. Adding the concentrate biological inoculant,
i3. Optionally provide one or more compatible treatments selected from:
  i3.1 Treatments with fungicides, insecticides and/or herbicides compatible with mycorrhizal forming fungi,
  i3.2 Treatment with beneficial microorganisms,
  i3.3 Treatment with macro and/or micronutrients,
  i3.4 Treatment with stimulants,
  i3.5 Treatment with colouring pigments compatible with mycorrhizal fungi;
i4. Drying the seeds.

Another object of the present invention is the use of a composition comprising *Dominikia* sp., deposited under accession number MUCL 57072 as bio-stimulant.

As used herein, the term "bio-stimulation" refer to the stimulation exerted by a composition according to the invention in plants that are provided with said composition.

Without being bound to a specific scientific explanation, it can be hypothesized that the *Dominikia* sp. strain of the invention exerts the function of translocation of nutrients, taking these nutrients from the soil or substrate and using said nutrients in its metabolic system, it translocates said nutrients from its mycelium network and it subsequently exchanges them in the root cells.

According to a preferred embodiment, the composition of the present invention is used as a bio-stimulant on cereals.

Another object of the present invention is the use of a composition comprising *Dominikia* sp., deposited under accession number MUCL 57072 as bio-nematicidal.

In other words, the composition of the present invention can be used to protect plants from nematodes.

According to a preferred embodiment, the composition of the present invention is used as a bio-nematicidal on cereals.

Advantageously, the composition of the invention can be provided to plants, i.e. to a crop, for example to a cereal crop, in several ways.

According to embodiments, the composition of the invention can be applied to the plant by seed treatment (i.e. seed coating), root treatment, roots embedded in an emulsion, addition to irrigation water, irrigation, application of powder to the root system or application of emulsion injected into the root system.

Preferably, in particular when it has to be provided to cereals, the composition of the invention is provided by seed coating or in conjunction with the seeds at the time of seeding, or in the form of microganulate and in conjunction with the seeds at the time of seeding.

EXPERIMENTAL SECTION

Example 1. Molecular Analyses

DNA—Extraction

Figure 1:
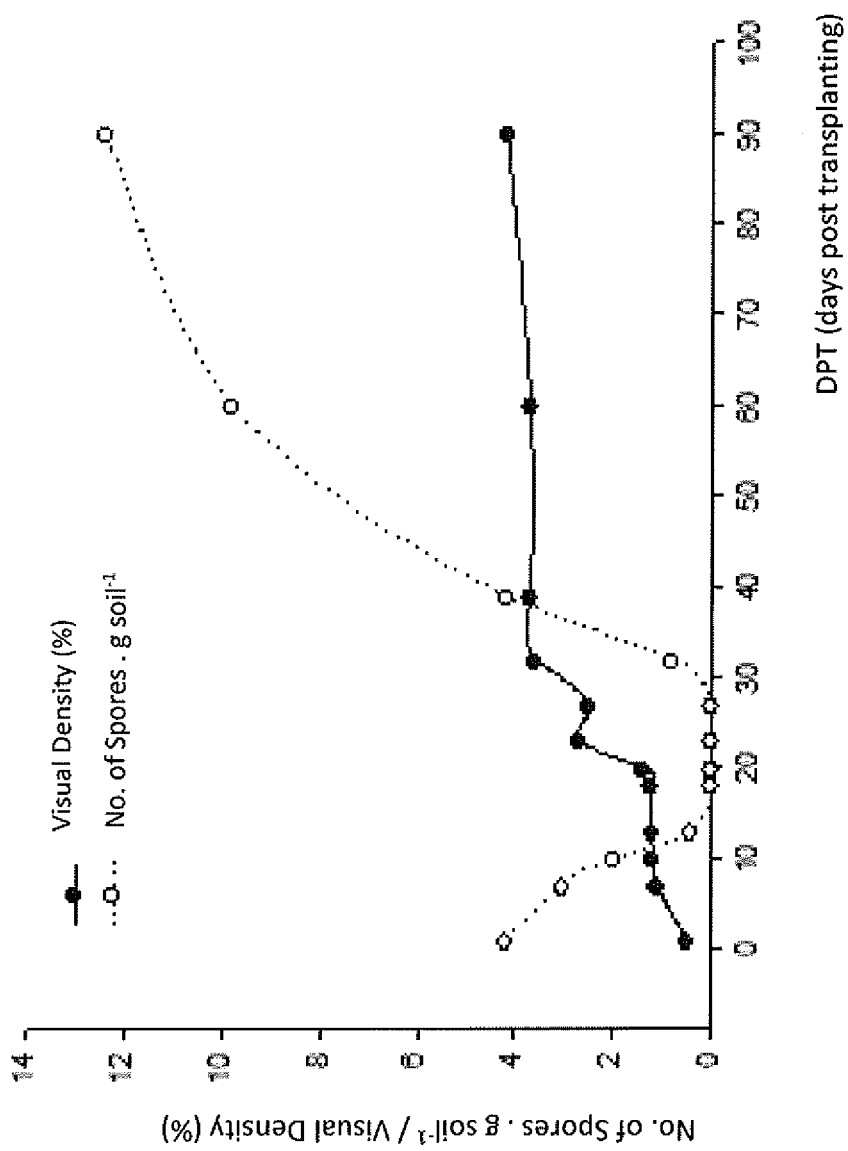
FIG. 1: Dynamics of spore production and fungal occupation, expressed through visual density (%), in plants treated with *Dominikia* sp.

Isolated hyphae and spores were transferred into 1.5 mL Eppendorf Tubes with 0.2 g of glass-beads (2 mm diameter) and 100 μL CTAB-buffer (2% CTAB=cetyltrimethylammoniumbromide, 1.4 M NaCl, 0.1 M Tris-HCl pH 7.5, 0.2 M Na-EDTA). This mixture was homogenized using a Retsch MM301 Ball Mill at 50 Hz for 30 seconds. Another 400 μL of CTAB-buffer were added and the mixture was incubated at 65° C. for one hour. 400 μL Cholroform-Isoamylalkohol (24:1) were added to the suspension and mixed by inverting the reaction tubes and subsequently centrifuged for 5 min at 15000×g and the top layer recovered into a clean Eppendorf tube. This step was repeated twice. To this suspension 200 μL 5 M Ammonium acetate were added; this mixture was incubated at 4° C. for at least 30 minutes followed by 20 minutes spinning at 4° C. and 15000×g. DNA was precipitated with 700 μL Isopropanol at −20° C. overnight. The DNA pellet obtained after Isopropanol-precipitation was washed with ice-cold 70% ethanol, air dried and re-dissolved in 50 μL TE buffer (10 mM Tris, 10 mM EDTA, pH 8)+4.5 U RNase/m L.

PCR-Conditons

The 18S rDNA was amplified using the primers GEOA2, GEO11 (Schwarzott D, Schüssler A (2001) A simple and reliable method for SSU rRNA gene DNA extraction, amplification, and cloning from single AM fungal spores. Mycorrhiza 10: 203-207), Primers used for PCR amplification and for sequencing of the 18S rDNA-internal transcribed spacer region were Glom1310 and ITS4i (Redecker D. (2000) Specific PCR primers to identify arbuscular mycorrhizal fungi within colonized roots. Mycorrhiza 10: 73-80). Amplifications were performed in 0.2 mM dNTP-mix, 1 mM of each primer, 10% of PCR reaction buffer and sterile, molecular grade water. GoTaq® DNA polymerase (Promega, Mannheim, Germany) was added at 4 u/100 μL of reaction mix; 2 μL of genomic DNA template were added in each 20 μL reaction. Amplifications were carried out in a Primus 96 advanced-thermocycler (peqLab Biotechnology) in 200 μL reaction tubes using the following PCR conditions: 96° C., 180 s initial denaturation; followed by 35 cycles: 96° C. 30 s, 58° C., 30 s, 72° C., 90 s; and a final extention at 72° C. for minutes.

Sequence Data and Glomeromycota Taxonomy

The reference alignment published by Kruger et al. (Kruger M, Kruger C, Walker C, Stockinger H, Schüßer A (2012) Phylogenetic reference data for systematics and phylotaxonomy of arbuscular mycorrhizal fungi from phylum to species level. New Phytol 193: 970-984; downloadable at www.amf-phylogeny.com) was used as basis for an 18S phylogeny. To identify similar environmental sequences the sequence of *Dominikia* sp. was blasted against GenBank and highly similar sequences were included in the alignment forming the basis of the 18S tree. Published partial 18S-ITS1-partial 5.8S sequences were used for the *Dominikia* phylogeny.

Data Analyses

Alignments were initially carried out by Clustal W. A maximum likelihood phylogenetic analysis was computed through the CIPRES web-portal (Miller MA, Pfeiffer W, Schwartz T. (2010) Creating the CIPRES Science Gateway for inference of large phylogenetic tres. In Proceedings of the Gateway Computing Environments Workshop (GCE), 14 Nov. 2010, New Orleans, LA pp 1-8; http://www.phylo.org/) with RAxML version 8.0 (Stamatakis et al. 2014) using 100 bootstrap replicates and the GTRGAMMA model. A Bayesian consensus tree was constructed using MrBayes version 2.0.5. Two separated MC3 runs with randomly generated starting trees were carried out for 2M generations each with one cold and three heated chains using the GTR+I model. All parameters were estimated from the data. Trees were sampled every 1000 generations. 200000 generations were discarded as "burn-in" and consensus trees constructed from the returning sample.

Example 2. Production Procedure of an Embodiment of the Composition of the Invention—Concentrated Composition for Seeds Coating First Phase—Greenhouse Conditions Substrate: Smectite clays are selected with pH between 7.8 and 8 and are sterilized in alternating cycles of 3 days before use as substrate.

AMF strain: *Dominikia* sp. propagules in pure conditions are used as started inoculum. This type of inoculant is always in continuous playback in cycles of 90-180 days, either in growth chamber or in greenhouses with controlled host plant conditions. Different plants are used to reproduce the inoculum in successive cycles to avoid disease transmission in the same host.

Summer—Fall: *Sorghum vulgare* and *Ocimum* sp.

Winter—Spring: *Lolium perenne*.

Culture Pots: Pots with 15 liter volume is used.

Growth Conditions of Host Plants:

In growth chamber or greenhouse, cultivation begins with the straight inoculation of the root system of the host plant with pure inoculum of the selected strain of arbuscular-mycorrhizal fungus (*Dominikia* sp.) in a sterile Smectite clay substrate. These plants are grown through their complete life cycle, according to the type of plant, taking between 90 and 180 days. The plants are always kept well hydrated, with a daily irrigation supply (Sterile water) with a temperature range between 25 and 28° C. and a relative humidity of 65%. Once completed, the root system is extracted, which contains smectite substrate, rootlets and pure AMF propagules, to be subsequently used to scale up in the second phase.

To determine the quality of the inoculum, the following minimum specifications are used:
Total Spores: 50-225 spores/g.
Extramatrical mycelium: >70 mg/kg substrate.
Rootlets colonized percentage: *Sorghum*>50%, *Lolium*>45%, *Ocimum*>40%.
MPN concentration: >1×10$^4$ propagules per 100 ml of substrate.

Second Phase—Scale Up
Step 1: Preparation of Beds

The beds are constructed with a plastic liner material so that the bed is isolated from surrounding soil; the beds are constructed so that the drainage occurs and the growth of undesired vegetation is prevented, preferably with a plastic covering.

Beds should be filled with the selected Smectite clay (Arcilla Roja Galve). The humidity of the clay should be approximately 15% to facilitate handling during bed filling. After filling irrigation should be provided to saturation to improve the structure.

Beds are located on well-drained sites.
Beds can have any dimensions, taking into consideration access required to facilitate the transit of people and equipment necessary for bed care.
Beds have irrigation system as dictated based on local needs. The preferred system setup may be either a drip irrigation or sprinkler and should be automated and allow independent watering of selected areas of the bed.

Step 2: Host Plant Species

Determination of host plant species and mycorrhizal fungi that can be set in the system: The selection and identification of the host plant and fungal species will correspond to the specific site conditions and objectives of the production. Rye grass (*Lolium perenne*) and the AMF previously produced at First Phase is used.

Step 3: Seeding the Host Plant and Inoculation

Prior to planting of the host plant, seed germination is tested. Based on the results of this test, the appropriate seeding rate is determined. In the case of perennial ryegrass seed is sown broadcast at 80 kg/ha of seed previously certified using pelleted seed. Also in conjunction with the seed 20 g of AMF inoculum m2 bed is applied directly to the Smectite clay.

Immediately after sowing irrigation is applied as a fine spray to prevent the redistribution of seed and inoculum.

The water used for irrigation should preferably have the following characteristics:
pH values of 6 to 7.5
Electrical conductivity: <1.6 mS/m
Soluble Total Salts: <1000 ppm
Sodium Absorption Ratio (SAR)<10
free of heavy elements and pathogens. It is preferred that the water used for irrigation is drinking water.

Step 4: Cultural Activities and Irrigation

Irrigation applied should be sufficient to achieve 100% of field capacity, but avoid applying too much water and causing ponding or standing water. Beds should be irrigated again when clay moisture drops to 75-80% of field capacity.

Step 5: Managing the Establishment of Mycorrhizal Symbiosis and Knowledge of the Dynamics of Development of the Colonization of Mycorrhizal Fungus.

During the growth and development of the host plant, AMF root colonization occurs and establishes the symbiosis between plant and fungus. To evaluate the development of this relationship, periodic sampling of roots system is conducted to evaluate the mycorrhizal development. Methods used to assess colonization include Gerdeman & Nicolson (1963) (Gerdemann J. W., Nicolson T. H. 1963. Spores of mycorrhizal endogen species extracted from soil by wet sieving and decanting. Transactions of the British Mycological Society 46(2):235-44), McGonigle (1990) (McGonigle, T. P., Miller M. H., Evans D. G., Fairchild G. L., Swan J. A. 1990. A new method which gives an objective measure of colonization of roots by vesicular arbuscular mycorrhizal fungi. New Phytologist 115 (3):495-501), and Phillips & Hayman (1970) (Phillips, J. M., Hayman D. S. 1970. Improved procedures for clearing roots and staining parasitic and vesicular arbuscular mycorrhizal fungi for rapid assessment of infection. Transactions of the British Mycological Society 55:158-161).

Sampling begins at two months after planting and continues monthly until the end of the growing season. With the information obtained from these samples the dynamics of development of mycorrhizal symbiosis within the inoculant can be determined.

Production process assessment is based on mycorrhizal root colonization, extrametrical concentration of mycelium, and spore content clay samples that are taken periodically.

Knowing the dynamics of mycorrhizal production development allows determination of the optimum harvest time and makes the most of the process of symbiosis on host plant and mycorrhizal fungus.

Step 6: Harvest

If the host plant that is used is the perennial *Lolium*, then the optimal harvest time normally occurs between 6 and 7 months after seeding, because in that period the plants mature, complete their life cycle and show a tendency to loss of vigor and become yellow.

Fifteen days before the scheduled harvest date the irrigation supply is eliminated and the foliage is maintained to allow the clay to lose moisture slowly ensuring completion of inoculation process. If this activity coincides with the rainy season, it will be necessary to protect the bed from the rain to allow it to dry in a timely manner, by covering the bed with waterproof plastic. Above ground foliage from host plants is first manually removed. Harvesting is done by removing clay from the bed. Remove the substrate by dividing the mass of clay on portions as thinly as possible to facilitate mixing their content throughout the depth of the profile and place it in the bags to transport.

Step 7: Dry and Milling of Inoculum

Drying: The harvested substrate and mycorrhizal propagules are subject to solarization and thermal disinfection for 30 days at 50° C. The drying period may be extended until a moisture content below 5%, in order to facilitate the milling process.

Milling: The product is ground in an industrial mill, cooled to 2° C. to prevent overheating mycorrhizal propagules. Grinding continues until a particle size of below 100 microns is achieved.

Third Phase—Concentration

After Step 7, the grounded biomass, it is come to the product concentration using a sieve of 35 microns. The particle obtained below of this measure (between 60-70% of the initial product) is discarded and stayed with the and to 30% of the ultra-concentrated product does not pass through that size and will be at the end, a concentrated composition. With the use of this technology we passed from $1.2 \times 10^4$ propagules per 100 ml to $1.2 \times 10^6$ propagules per 100 ml.

The outlet relative humidity of the product is below 5%.

Quality Control: The final product purity and concentration is determined following the most probable number method of Porter (1979) (Porter, W. M. 1979. The most probable number method for enumerating infective propagules of vesicular arbuscular mycorrhizal fungi in soils. Aust. J. Soil Res. 17:515-519).

Packaging: Finished product is packaged and labeled for shipment.

The final concentration of the concentrate composition is:
MPN concentration: $>1.2 \times 10^6$ propagules per 100 ml of product. Fourth Phase—Seed Coating Coating the seeds with mycorrhizal inoculant can be performed in a special machine for coating seeds, in a conventional concrete mixer or manually in a mixing vessel. Said coating requires various steps that are described below in the order in which they are performed.

1. As an initial step, the seeds are coated with an adhesive substance. The adhesive substances that can possibly be used in addition to water include organic adhesives (gelatin, ethyl cellulose, propylene glycol, etc.) and inorganic adhesives (mineral oils, polyvinyls, plastic resins, etc.). The preferred adhesives used are polymeric or copolymeric of the polyvinyl group such as polyvinylpyrrolidone and polyvinyl acetate. The adhesive is added to an aqueous or alcoholic solution to its optimal solubility, varying the amount of adhesive used between 0.1% and 15%, preferably between 0.5% and 10% and still more preferably between 1.0% and 5% of the total weight of the seeds to be coated. The amount of adhesive used will depend on its chemical properties as well as the type of seed to be treated. The time of treatment of the seeds with the adhesive may vary between 1 and 60 seconds, preferably between 5 and 50 seconds and still more preferably between 10 and 40 seconds per 100 kg of seeds used.

2. After coating with adhesive, the mycorrhizal inoculant is then added. The proportion of the inoculant added to the seeds may be selected in the range between 0.1% and 15%, preferably between 0.5% and 10% and still more preferably between 1% and 5% of the weight of seeds, which will depend on the type and variety. The time of treatment of the seeds with the mycorrhizal inoculant may vary between 1 and 50 seconds, preferably between 5 and 40 seconds and still more preferably between 10 and 30 seconds per 100 kg of seeds used.

The mycorrhizal treatment may be combined with other treatments that are described in sections 2a to 2e. These treatments may also be performed independently of the mycorrhizal inoculant treatment, obtaining a multi-layer coating. The steps to be performed in the coating of each layer are the same as those in the case of the mycorrhizal inoculant. These layers may be separated by coating the seeds with innocuous substances of calcareous (calcium carbonate and similar), clay or polymeric origins. The pelletizing or encrusting substance must not exceed 50%, preferably 40% and still more preferably 30% of the weight of the seed and is added to the seed with an adhesive substance as mentioned in section 1.

2a. Treatments with fungicides, insecticides and/or herbicides compatible with mycorrhizal forming fungi. In general terms, all commercial herbicides and insecticides are compatible with mycorrhizal forming fungi. However, not all fungicides are compatible with the survival of mycorrhizal fungi. The main fungicides to be used include azoxystrobin, carboxin, cyproconazole, chlorothalonil, metalaxyl, myclobutanil and prothioconazole. The amount of pesticide used will depend on the manufacturer's recommendations and various pesticides can be used depending on the need.

2b. Treatment with beneficial microorganisms including *Trichoderma* spp., *Rhizobium* bacteria and/or a combination of microorganisms beneficial to the rhizosphere such as *Aspergillus, Penicillium* and nitrogen fixing bacteria.

2c. Treatment with macro and/or micronutrients, where nitrogen (N), phosphorus (P), potassium (K), calcium (Ca), magnesium (Mg) and sulphur (S) are the essential macronutrients and iron (Fe), zinc (Zn), manganese (Mn), boron (B), copper (Cu), molybdenum (Mo) and chlorine (Cl) are the essential micronutrients. The dose of nutrients for coating may vary between and 15%, preferably between 0.05% and 10%, and still more preferably between 0.1% and 5% of the total weight of the seeds to be coated.

2d. Treatment with stimulants. Coating the seeds with stimulants that induce seed germination and growth and plant defence and sporulation and mycorrhizal fungal growth. The stimulants can be phytohormones (abscisic acid, strigolactones, brassinosteroids, etc.) and their inducers and derivatives, secondary metabolites (flavonoids, terpenoids, etc.) and cofactors (metal ions, etc.).

2e. Treatment with colouring pigments: these pigments must be compatible with the survival of the mycorrhizal fungus and be a clear differentiator between treated and non-treated seeds.

3. Steps 1 and 2 mean that a complete coating of the mycorrhizal inoculant by the adhesive substance is performed in a time of from 1 to 40 seconds, preferably from 5 to 30 seconds and still more preferably from 10 to 20 seconds, performing a complete coating of the mycorrhizal inoculant by the adhesive substance.

4. After performing the mycorrhizal treatment, the seeds are dried for a time that can vary between 1 and 50 seconds, preferably between 5 and 40 seconds and still more preferably between 10 and 30 seconds. This step may be performed after step 5.

5. Finally the coated seeds are discharged into containers from the coating component. The duration of the discharge may vary from 5 to 30 seconds, preferably from 10 to 25 seconds and still more preferably from 15 to 20 seconds.

Example 3. Production Procedure of an Embodiment of the Composition of the Invention—Micro Granulated Composition First Phase—Greenhouse Conditions Substrate: Smectite clays are selected with pH between 7.8 and 8 and are sterilized in alternating cycles of 3 days before use as substrate.

AMF strain: *Dominikia* sp. propagules in pure conditions are used as started inoculum. This type of inoculant is always in continuous playback in cycles of 90-180 days, either in growth chamber or in greenhouses with controlled host plant conditions. Different plants are used to reproduce the inoculum in successive cycles to avoid disease transmission in the same host.

Summer—Fall: *Sorghum vulgare* and *Ocimum* sp.
Winter—Spring: *Lolium perenne*.
Culture Pots: Pots with 15 liter volume is used.

Growth Conditions of Host Plants:

In growth chamber or greenhouse, cultivation begins with the straight inoculation of the root system of the host plant with pure inoculum of the selected strain of arbuscular-mycorrhizal fungus (*Dominikia* sp.) in a sterile smectite clay substrate. These plants are grown through their complete life cycle, according to the type of plant, taking between 90 and 180 days. The plants are always kept well hydrated, with a daily irrigation supply (Sterile water) with a temperature range between 25 and 28° C. and a relative humidity of 65%. Once completed, the root system is extracted, which contains smectite substrate, rootlets and pure AMF propagules, to be subsequently used to scale up in the second phase.

To determine the quality of the inoculum, the following minimum specifications are used:
Total Spores: 50-225 spores/g.
Extramatrical mycelium: >70 mg/kg substrate.
Rootlets colonized percentage: *Sorghum*>50%, *Lolium*>45%, *Ocimum*>40%.
MPN concentration: >$1\times10^4$ propagules per 100 ml of substrate.

Second Phase—Scale Up
Step 1: Preparation of Beds

The beds are constructed with a plastic liner material so that the bed is isolated from surrounding soil; the beds are constructed so that the drainage occurs and the growth of undesired vegetation is prevented, preferably with a plastic covering.

Beds should be filled with the selected Smectite clay (Arcilla Roja Galve). The humidity of the clay should be approximately 15% to facilitate handling during bed filling. After filling irrigation should be provided to saturation to improve the structure.

Beds are located on well-drained sites.

Beds can have any dimensions, taking into consideration access required to facilitate the transit of people and equipment necessary for bed care.

Beds have irrigation system as dictated based on local needs. The preferred system setup may be either a drip irrigation or sprinkler and should be automated and allow independent watering of selected areas of the bed.

Step 2: Host Plant Species

Determination of host plant species and mycorrhizal fungi that can be set in the system: The selection and identification of the host plant and fungal species will correspond to the specific site conditions and objectives of the production. Rye grass (*Lolium perenne*) and the AMF previously produced at First Phase is used.

Step 3: Seeding the Host Plant and Inoculation

Prior to planting of the host plant, seed germination is tested. Based on the results of this test, the appropriate seeding rate is determined. In the case of perennial ryegrass seed is sown broadcast at 80 kg/ha of seed previously certified using pelleted seed. Also in conjunction with the seed 20 g of AMF inoculum m2 bed is applied directly to the Smectite clay.

Immediately after sowing irrigation is applied as a fine spray to prevent the redistribution of seed and inoculum.

The water used for irrigation should preferably have the following characteristics:
pH values of 6 to 7.5
Electrical conductivity: <1.6 mS/m
Soluble Total Salts: <1000 ppm
Sodium Absorption Ratio (SAR)<10
free of heavy elements and pathogens. It is preferred that the water used for irrigation is drinking water.

Step 4: Cultural Activities and Irrigation

Irrigation applied should be sufficient to achieve 100% of field capacity, but avoid applying too much water and causing ponding or standing water. Beds should be irrigated again when clay moisture drops to 75-80% of field capacity.

Step 5: Managing the Establishment of Mycorrhizal Symbiosis and Knowledge of the Dynamics of Development of the Colonization of Mycorrhizal Fungus.

During the growth and development of the host plant, AMF root colonization occurs and establishes the symbiosis between plant and fungus. To evaluate the development of this relationship, periodic sampling of roots system is conducted to evaluate the mycorrhizal development. Methods used to assess colonization include Gerdeman & Nicolson (1963) (Gerdemann J. W., Nicolson T. H. 1963. Spores of mycorrhizal endogone species extracted from soil by wet sieving and decanting. Transactions of the British Mycological Society 46(2):235-44), McGonigle (1990) (McGonigle, T. P., Miller M. H., Evans D. G., Fairchild G. L., Swan J. A. 1990. A new method which gives an objective measure of colonization of roots by vesicular arbuscular mycorrhizal fungi. New Phytologist 115 (3):495-501), and Phillips & Hayman (1970) (Phillips, J. M., Hayman D. S. 1970. Improved procedures for clearing roots and staining parasitic and vesicular arbuscular mycorrhizal fungi for rapid assessment of infection. Transactions of the British Mycological Society 55:158-161).

Sampling begins at two months after planting and continues monthly until the end of the growing season. With the information obtained from these samples the dynamics of development of mycorrhizal symbiosis within the inoculant can be determined.

Production process assessment is based on mycorrhizal root colonization, extrametrical concentration of mycelium, and spore content clay samples that are taken periodically.

Knowing the dynamics of mycorrhizal production development allows determination of the optimum harvest time and makes the most of the process of symbiosis on host plant and mycorrhizal fungus.

Step 6: Harvest

The harvest is the most critical step in the production process. If the host plant that is used is the perennial *Lolium*, then the optimal harvest time normally occurs between 6 and 7 months after seeding, because in that period the plants mature, complete their life cycle and show a tendency to loss of vigor and become yellow.

Fifteen days before the scheduled harvest date the irrigation supply is eliminated and the foliage is maintained to allow the clay to lose moisture slowly ensuring completion of inoculation process. If this activity coincides with the rainy season, it will be necessary to protect the bed from the rain to allow it to dry in a timely manner, by covering the bed with waterproof plastic.

Above ground foliage from host plants is first manually removed. Harvesting is done by removing clay from the bed. Remove the substrate by dividing the mass of clay on portions as thinly as possible to facilitate mixing their content throughout the depth of the profile and place it in the bags to transport.

Step 7: Dry and Milling of Inoculum

Drying: The harvested substrate and mycorrhizal propagules are subject to solarization and thermal disinfection for 30 days at 50° C. The drying period may be extended until a moisture content below 5%, in order to facilitate the milling process.

Milling: The product is ground in an industrial mill, cooled to 2° C. to prevent overheating mycorrhizal propagules. Grinding continues until a particle size of below 100 microns is achieved.

Third Phase—Micro Granulation

The Micro Granulation Process is Divided in Three Steps:

Addition of granular support into the rotating biconical mixer. To produce the support was used: Mix of mica, attapulgite and limestone in a range between 40-90% by weight, more preferably between 50-80% by weight, even more preferably between 60-70 by weight.

Addition of mycorrhizae (arbuscular mycorrhizal fungus): the AMF is dosed between 10-60% by weight, more preferably between 20-50% by weight, even more preferably between 30-40% by weight of *Dominikia* sp. previously produced (Step 7) along with a binder (wax, linseed oil, gum arabic, gum tragacanth, methyl cellulose, polyvinyl alcohol, tapioca flour, lactose, sucrose, microcrystalline cellulose, poly vinyl pyrrolidone, lactose powder, sucrose powder, tapioca starch (cassava flour) and microcrystalline cellulose, gums, or protein such as egg white or casein) in a range of 1 to 25% by weight, more preferably of 5 to 20% by weight, even more preferably of 10 to % by weight inside the rotating biconical mixer by a screw. During this operation, the mixer is kept moving until total granule homogenization.

Packaging: once the formulated product is totally homogenized it is discharged onto a sieve to remove clumps and dust produced. Finally, the product is collected in a packaging hopper from which automatically proceeds to give the corresponding filling containers.

Quality Control and Packaging

Quality Control: The final product purity and concentration is determined following the most probable number method of Porter (1979) (Porter, W. M. 1979. The most probable number method for enumerating infective propagules of vesicular arbuscular mycorrhizal fungi in soils. Aust. J. Soil Res. 17:515-519).

Packaging: Finished product is packaged and labeled for shipment.

The final concentration of the microgranulated composition is:

MPN concentration: >1×10$^4$ propagules per 100 ml of product.

Example 4. Effect of the Composition of the Invention on the Development of Wheat (*Triticum durum*)

In order to demonstrate the effectiveness of the composition of the present invention, which comprises the arbuscular mycorrhizal fungus (AMF) *Dominikia* sp., deposited under accession number MUCL 57072 on wheat, a trial was conducted in the experimental field "Tres cam inos", property of CEBAS-CSIC in Murcia.

The experimental design was randomized block with four replications. The experimental plots were 3 m long per 4.2 m wide.

The following treatments were applied:

Control: no chemical fertilization and no fungus applied

Composition of the invention: provided in microgranulated form, with a rate of 10 kg/ha, in combination with chemical fertilization (Guerra, B. E. Micorriza arbuscular. Recurso microbiológico en la agricultura sostenible. Tecnologia en Marcha, 2008, vol. 21, no. 1, p. 191-201).

Standard product: chemical fertilization (Guerra, B. E. Micorriza arbuscular. Recurso microbiológico en la agricultura sostenible. Tecnologia en Marcha, 2008, vol. 21, no. 1, p. 191-201): 150 kg/ha of nitrogen, 54 kg/ha of phosphorus, 100 kg/ha of potassium, 15 kg/ha of calcium, 15 kg/ha of magnesium, 23 kg/ha of sulphur and other micronutrients.

Planting was done on 1 Nov. 2013 and the harvest took place on Jun. 1, 2014, for a total of 240 days. The type of sowing and inoculation used was mechanical and was applied by a grain drill stroke and the composition of the invention, in microgranulated form, was applied at 10 kg/ha along with the seed.

The soil used was classified as Nitisol (IUSS Working Group. WRB. World reference base for soil resources 2006. World Soil Resources Reports. Rome: FAO, 2006). For chemical characterization of the soil the following analytical methods were used:

pH: soil-solution ratio 1:2.5.

Organic matter (MO): Walkley and Black.

$P_2O_5$: Oniani.

Exchangeable cations: extraction with $NH_4$ AC at 1 mol/L at pH 7 and complexometric titration (Ca and Mg) and flame photometry (Na and K).

These methods are described in the manual of analytical techniques for the analysis of soil, foliar, organic fertilizers and chemical fertilizers (Instituto Nacional de Ciencias Agricolas. Manual de tecnicas Analiticas para analisis de suelo, foliar, abonos organicos y fertilizantes quimicos: La Habana. 1989). The results of chemical soil characteristics (Table 2) show a medium to high fertility, noting an average content of organic matter, which respond to that described for this type of soil (Hernandez, A.; Morell, F.; Ascanio, M. O.; Borges, Y.; Morales, M. y Yong, A. Cambios globales de los suelos Ferraliticos Rojos Lixiviados (Nitisoles Ródicos Éutricos) de la provincia La Habana. Cultivos Tropicales, 2006, vol. 27. no. 2, p. 41-50).

TABLE 2

| Chemical characteristics of soil. | |
|---|---|
| Organic matter (%) | 3.21 |
| pH | 7.02 |
| $P_2O_5$ | 397.25 |
| K (cmol/kg soil) | 0.96 |
| Ca (cmol/kg soil) | 14.26 |
| Mg (cmol/kg soil) | 3.70 |
| Na (cmol/kg soil) | 0.11 |

The fungal strain of the invention of *Dominikia* sp. was isolated from a saline soil, this fungus is tolerant to high salt concentrations.

The variables analyzed were: the number of spores of AMF per gram of rhizospheric soil (Gederman, J. W. y Trappe, J. M. The endogonaceae in the pacific northwest. Mycologia Memoir No 5. The New York Botanic Garden.

1974, no. 5), the percentage of mycorrhizal colonization by the technique of staining of the roots (Phillips, J. M. y Hayman, D. S. Improved procedures for clearing roots and staining parasitic and vesicular arbuscular mycorrhizal fungi for rapid assessment of infection. Tranfer. Britanic: Mycology Society, 1970, vol. 55, p. 158-161), the percentage of visual density through the intercepts method (Giovannetti, M. y Mosse, B. An evaluation of techniques to measure vesicular—arbuscular infection in roots. New Phytology, 1980, vol. 84, p. 489-500) and the total glomalin (glycoprotein) content which was obtained by the pressure cooker method (Wright, S. E.; Nichols, K. A. y Schmidt, W. F. Comparison of efficacy of three extractants to solubilize glomalin on hyphae and in soil. Chemosphere, 2006, vol. 64, no. 7, p. 1219-1224).

Foliar nutrients content (% N, P and K) and the total protein content were determined by the methods described in the laboratory manual of analytical techniques of INCA (Instituto Nacional de Ciencias Agricolas. Manual de tecnicas Analiticas para analisis de suelo, foliar, abonos orgánicos y fertilizantes quimicos: La Habana. 1989).

The yield was evaluated as follows: the number of grains per spike were evaluated; number of spike per $m^2$; mass per 1000 grains and agricultural yields (T/ha).

The statistical processing of the experimental results was done by analysis of one way ANOVA and test of Duncan (Duncan, D. B. Multiple range and multiple F tests. Biometrics, 1955, vol. 11, no. 1) was used, when there were differences between treatment means statistical processor SPSS 11.5 was used in all cases.

Results and Discussion

Table 3 shows the results of the different treatments on the mycorrhizal variables. These values clearly showed an increased number of spores where the composition of the invention was applied in relation with the control (no chemical fertilization) and with the standard product.

TABLE 3

Effect of treatments on mycorrhizal variables studied.

| Treatments | Spores/gram of soil | Colonization (%) | VD (%) | Glomalin (mg/g soil) |
|---|---|---|---|---|
| Control | 42 b | 12.3 b | 0.12 b | 1.8 b |
| Composition of the invention | 156 a | 65.3 a | 3.25 a | 9.27 a |
| Standard product | 36 b | 11.2 b | 0.11 b | 1.78 b |
| P | 0.014** | 0.04*** | 0.021** | 0.017** |
| F | 8.5 | 9.2 | 7.1 | 6.5 |

*Different letters in the same column are significantly different at $p < 0.05$.

The above it may be due to a strong colonization activity, making difficult the root colonization by other species of arbuscular mycorrhizal fungi. On the other hand, it shows that mycorrhizal colonization was also more effective with the composition of the invention reflecting higher values compared to other treatments.

It should be noted that native strains in soil showed low values of colonization. By observing the values of visual density (variable measuring the intensity of mycorrhizal colonization), shows that the highest percentage was obtained with the composition of the invention.

Another variable to highlight was total glycoprotein content which was higher with the composition of the invention. This phenomenon reaffirms a greater mycorrhizal symbiosis when the composition of the invention is applied and the possible influence of the inoculant to increase the formation of aggregates in the soil. Moreover, treatments where mycorrhizal inoculant was not applied had low values of this variable, which may be attributable to the low effectivity of native mycorrhizae.

Table 4 shows the foliar mineral contents on each treatment. For nitrogen and phosphorus the content was higher where the composition of the invention was applied while the sodium content was higher for the chemical fertilization.

TABLE 4

Foliar nitrogen, phosphorus, potassium and total protein.

| Treatments | % N | % P | % K | Total protein (%) |
|---|---|---|---|---|
| Control | 1.25 b | 0.26 b | 1.12 | 8.04 b |
| Composition of the invention | 1.45 a | 0.40 a | 1.18 | 10.1 a |
| Standard product | 1.41 a | 0.36 a | 1.23 | 9.89 a |
| P | 0.001** | 0.023** | 1.23 ns | 0.013* |
| F | 7.2 | 5.6 | 8.8 | 6.5 |

*Different letters in the same column are significantly different at $p < 0.05$.

It should be noted that reported values (López-Bellido, L. Cultivos herbáceos. Cerealés. Ed. Mundi-Prensa, 1991. p. 151-158) for this variable (% N foliar) are above the critical index of wheat yields between 4 and 5 T/ha.

Similar results (Cornejo, P.; Borie, F.; Rubio, R. y Azcon, R. Influence of nitrogen source on the viability, functionality and persistence of *Glomus etunicatum* fungal propagules in an Andisol. Applied Soil Ecology, 2007, vol. no. 2, p. 423-431; Echeverria, E. y Stiddert, G. A. El contenido de nitrógeno en la hoja bandera del trigo como predictivo del incremento de proteina en el grano por aplicaciones de nitrógeno en la espigazón (The nitrogen content in the wheat flag leaf as predictive of the increase in protein in the grain by nitrogen applications to the ear). Revista de la Facultad de Agronomia, 1998, vol. 103, no. 1, p. 10) indicate the presence of this nutrient in leaf tissue, due to mycorrhizal symbiosis process which allows the absorption and transport of nutrients through the mycelia. The content of foliar phosphorus did not show significant differences for any of the treatments, which may be due to the content of this element on soil (Table 4), which is taken up by plants from the soil solution through its radical and system, in this particular case by the tripartite interaction plant-arbuscular mycorrhizal (mycorrhizal symbiosis) and soil, pointing out a higher value than the foliar critical index of this nutrient in durum wheat (López-Bellido, L. Cultivos herbáceos. Cereales. Ed. Mundi-Prensa, 1991. p. 151-158) and indicating a good crop development. As well as this value was higher trend where the composition of the invention was applied.

Another variable that is relevant is the foliar protein content, which is higher in the treatment with the composition of the invention (even higher than treated with chemical fertilization). Finally, the control treatment had a significant lower percentage.

The results of yield and its components (Table 4) reflect clearly the response of durum wheat to the application of the composition of the invention and standard product, both with high contents of N.

TABLE 5

Effect of treatments on yield and its variables.

| Treatments | Grains/spike | No spikes/m² | Mass of 1000 grains (g) | Yield (T/ha) | Increase (%) |
|---|---|---|---|---|---|
| Control | 25.00 b | 576 | 29.0 b | 3.25 b | — |
| Composition of the invention | 33.00 a | 641 | 33.4 a | 5.22 a | 8.8 |
| Standard product | 30.00 a | 635 | 32.0 a | 4.60 a | — |
| P | 0.02** | 11.25 ns | 0.015* | 0.009** | |
| F | 11.2 | 10.2 | 6.1 | 7.8 | |

*Different letters in the same column are significantly different at $p < 0.05$.

Treatments with the composition of the invention and standard product gave the highest values on each variable with respect to the control. It could be explained by greater effectiveness of the solid inoculant and the application of high doses of nitrogen.

It is good to note that wheat cultivation associated with the composition of the invention, allowed to achieve adequate productive response with acceptable indicators of mycorrhizal operation, not only to improve soil biological activity, but promoted a significant increase production of 8.8% in relation to the control and the standard product.

Example 5. Effect of the Composition of the Invention on the Development of Corn (*Zea mays*)

In order to demonstrate the effectiveness of the composition of the invention, which comprises the arbuscular mycorrhizal fungus (AMF) *Dominikia* sp., deposited under accession number MUCL 57072, on maize, a trial was conducted on a field close to the town Egea de los Caballeros. A microgranular form of the composition of the invention was tested. A standard product was used to compare the effect of both products on the cultivation of maize, var DKC 6717, Monsanto; on a Cambisol soil.

Planting was done on 12 April and the harvest took place on Dec. 14, 2014, for a total of 230 days. The type of sowing and inoculation used was mechanical and was applied by a grain drill stroke and the microgranulate composition of the invention was applied at 10 kg/ha along with the seed. The planting used was 0.7 m×0.16 m for a total of 80 plants per square meter. The spray system used was 18×18 m.

The experimental design was randomized block with three replications. The experimental plots were 20 m long× 20 m wide.

The following treatments were applied:
Composition of the invention: provided at 10 kg/ha and chemical fertilization (Guerra, B. E. Micorriza arbuscular. Recurso microbiológico en la agricultura sostenible. Tecnologia en Marcha, 2008, vol. 21, no. 1, p. 191-201).
Standard product: chemical fertilization (Guerra, B. E. Micorriza arbuscular. Recurso microbiológico en la agricultura sostenible. Tecnologia en Marcha, 2008, vol. 21, no. 1, p. 191-201): 325 kg/ha of nitrogen, 80 kg/ha of phosphorus and 200 kg/ha of potassium, with an initial contribution of organic matter in the form of slurry 10 T/ha.

The soil used was classified as Cam bisol (IUSS Working Group. WRB. World reference base for soil resources 2006. World Soil Resources Reports. Rome:FAO, 2006). For chemical characterization of the soil the following analytical methods were used:

pH: soil-solution ratio 1:2.5.
Organic matter (MO): Walkley and Black.
$P_2O_5$: Oniani.
Exchangeable cations: extraction with $NH_4$ AC at 1 mol/L at pH 7 and complexometric titration (Ca and Mg) and flame photometry (Na and K).

These methods are described in the manual of analytical techniques for the analysis of soil, foliar, organic fertilizers and chemical fertilizers (Instituto Nacional de Ciencias Agricolas. Manual de técnicas Analiticas para análisis de suelo, foliar, abonos organicos y fertilizantes quimicos: La Habana. 1989). The results of chemical soil characteristics (Table 6) show a medium to high fertility, noting an average content of organic matter, which respond to that described for this type of soil (Hernandez, A.; Morell, F.; Ascanio, M. O.; Borges, Y.; Morales, M. y Yong, A. Cambios globales de los suelos Ferraliticos Rojos Lixiviados (Nitisoles Ródicos Éutricos) de la provincia La Habana. Cultivos Tropicales, 2006, vol. 27. no. 2, p. 41-50).

TABLE 6

Chemical characteristics of soil

| | |
|---|---|
| Organic matter (%) | 2.51 |
| pH | 8.02 |
| $P_2O_5$ | 258.60 |
| K (cmol/kg soil) | 1.40 |
| Ca (cmol/kg soil) | 15.44 |
| Mg (cmol/kg soil) | 2.90 |
| Na (cmol/kg soil) | 0.30 |

The fungal strain of the invention of *Dominikia* sp. was isolated from a saline soil, this fungus is tolerant to high salt concentrations.

The variables analyzed were: percentage of mycorrhizal colonization by the technique of staining of the roots (Phillips, J. M. y Hayman, D. S. Improved procedures for clearing roots and staining parasitic and vesiculararbuscular mycorrhizal fungi for rapid assessment of infection. Tranfer. Britanic: Mycology Society, 1970, vol. 55, p. 158-161) and percentage of visual density (VD) through the intercepts method (Giovannetti, M. y Mosse, B. An evaluation of techniques to measure vesicular—arbuscular infection in roots. New Phytology, 1980, vol. 84, p. 489-500). Foliar nutrients content (% N, P and K) were determined by the methods described in the laboratory manual of analytical techniques (Instituto Nacional de Ciencias Agricolas. Manual de técnicas Analiticas para analisis de suelo, foliar, abonos orgánicos y fertilizantes quimicos: La Habana. 1989).

The yield was evaluated as follows: the number of grains per spike were evaluated; number of spike per square meter; mass per 1000 grains and agricultural yields (T/ha).

The statistical processing of the experimental results was done by analysis of one way ANOVA and test of Duncan (Duncan, D. B. Multiple range and multiple F tests. Biometrics, 1955, vol. 11, no. 1) was used, when there were differences between treatment means statistical processor SPSS 11.5 was used in all cases.

Results and Discussion

Table 7 shows the results of the mycorrhizal activity evolution at 45 and 120 days after planting. These values clearly showed an increased activity where the composition of the invention was applied, reaching not only a greater mycorrhizal colonization percentage, but also a greater intensity of colonization, reflected through higher visual density.

TABLE 7

Effect of treatments on mycorrhizal variables studied.

| | Colonization (%) 45 days | Colonization (%) 120 days | VD (%) 45 days | VD (%) 120 days |
|---|---|---|---|---|
| Composition of the invention | 36.2 a | 64.12 a | 3.4 a | 4.28 a |
| Standard Product | 10.1 b | 11.36 b | 0.3 b | 0.85 b |
| P | 0.011** | 0.02*** | 0.01* | 0.006* |
| F | 7.2 | 8.2 | 8.1 | 9.4 |

*Different letters in the same column are significantly different at $p < 0.05$.

This assay showed that the most effective inoculant was the composition of the invention, which reflected higher values compared to other treatments. The values of visual density (variable which measures the intensity of the mycorrhizal colonization), shows that the highest percentage was also related to the composition of the invention, closely related to the effectiveness.

Foliar mineral contents were measured (Table 8). The results showed no significant differences between both treatments, the composition of the invention and standard product. However there was a trend to a greater nutritional supply, especially in the case of nitrogen content in the presence of *Dominikia* sp. (composition of the invention).

TABLE 8

Foliar nitrogen, phosphorus, potassium at 120 days on maize.

| Treatments | % N | % P | % K |
|---|---|---|---|
| Composition of the invention | 1.48 | 0.41 | 1.81 |
| Standard product | 1.40 | 0.35 | 1.9 |
| P | 0.12 ns | 0.1 ns | 0.22 ns |
| F | 8.5 | 8.2 | 7.9 |

*Different letters in the same column are significantly different at $p < 0.05$.

It should be noted that nitrogen content values obtained with the treatment with the composition of the invention are above the critical index of wheat for production yields between 4 and 5 T/ha (López-Bellido, L. Cultivos herbáceos. Cereales. Ed. Mundi-Prensa, 1991. p. 151-158).

The content of foliar phosphorus did not show significant differences for any of the treatments, which may be due to the content of this element on the soil used (Table 8). Phosphorus is taken up by plants through its radical system, in this particular case by the tripartite interaction plant-arbuscular mycorrhizal (mycorrhizal symbiosis) and soil. The foliar phosphorus content was higher than the critical index of this nutrient in durum wheat (López-Bellido, L. Cultivos herbáceos. Cereales. Ed. Mundi-Prensa, 1991. p. 151-158) which indicate a good crop development. However this value was higher trend in the treatment treated with the composition of the invention.

Similar results in wheat and maize demonstrate the effect of mineral fertilization on the percentage of length of colonized roots, where low doses of phosphorus were applied. This support the importance and usefulness of the composition of the invention for corn and wheat plants to increase the absorption of phosphorus from the soil in either presence or absence of nitrogen and phosphorus, which allows to minimize the dose fertilizer to apply.

Foliar potassium contents were similar for the different treatments under study, showing satisfactory levels for this crop, which coincides with the statements for cereals about this macro element (López-Bellido, L. Cultivos herbáceos. Cereales. Ed. Mundi-Prensa, 1991. p. 151-158). Moreover, high concentrations of this element are found in both mycorrhizal plants and those that are not (Bolleta, A. y Krugger, H. Fertilización e inoculacion con hongos micorrizicos arbusculares en trigo. Buenos Aires:Instituto Nacional de Tecnologia Agropecuaria. 2004, Saleque, M. A.; Timsina, J.; Panaullah, G. M.; Ishaque, M.; Pathan, D. J.; Saha, P. K.; Quayyum, M. A.; Humphreys, E. y Meisner, C. A. Nutrient uptake and apparent balances for rice-wheat sequences. II. Phosphorus. Journal of Plant Nutrition, 2006, vol. 29, no. 1, p. 157-172), which may be due to the fact that this element moves more easily in the soil solution.

The following table sum up the results obtained (Table 9), which clearly reflect the maize response to the application of the composition of the invention and to the standard product.

TABLE 9

Effect of treatments on yield and its components in the culture.

| Treatments | Yield (kg/ha) | Grain humidity (%) | Increase (%) |
|---|---|---|---|
| Composition of the invention | 14700.2 a | 22 | 9.18 |
| Standard Product | 13500.3 b | 20 | — |
| P | 0.042** | | |
| F | 29.40 | | |

*Different letters in the same column are significantly different at $p < 0.05$.

Plants treated with the composition of the invention reached the highest values in comparison with the standard product, which could be explained by a greater effectiveness of the solid inoculant to establish a symbiosis with the plant and thus a better assimilation of high doses of nitrogen.

Finally and in conclusion is good to point out that maize cultivation associated with the composition of the invention, allowed to achieve a positive production response from the point of view of performance, reaching a production increase of 9.18% compared to mineral fertilization. As well as, nutritional indicators showed a higher trend and the use of arbuscular mycorrhizal fungus of the invention not only improve soil biological activity, but promoted a significant increase in production based on a more sustainable management.

Example 6. Effectiveness of Coating Corn Seed with *Dominikia* sp. and an Adhesive Substance on the Mycorrhizal Activity Objective: To learn about the efficacy of coating corn with *Dominikia* sp. and an adhesive substance on the mycorrhizal activity.

To achieve this objective, three planters (each considered a repetition) were planted with corn seeds coated with *Dominikia* sp. deposited under accession number MUCL 57072 and an adhesive substance.

The seeds were planted on Aug. 3, 2016 and mycorrhizal colonisation assays were performed on the root using the Phillips and Hayman, 1970, staining technique at 21 and 35 days after planting.

TABLE 10

Percentage of mycorrhizal colonisation (% MC) of the rootlets from corn seeds coated with the combination of *Dominikia* sp. and an adhesive substance at 21 and 35 days post planting (dpp) respectively.

| Date of evaluation | Planter 1 (% MC) | Planter 2 (% MC) | Planter 3 (% MC) | Mean (X) |
|---|---|---|---|---|
| 28 Mar. 2016 (21 dpp) | 7 | 9 | 10 | 8.6 |
| 10 Oct. 2016 (35 dpp) | 12 | 11 | 15 | 12.6 |

Table 10 shows that in each of the samples analysed, there was a positive mycorrhizal colonisation percentage, which increased as the plants were growing. At this stage, only incipient colonisation points on the corn were detected, formed by the network of extramatrical mycelium that had just begun to form.

Conclusions:

The coating of the corn seed with the concentration of inoculant containing *Dominikia* sp. and an adhesive substance was effective because it generated mycorrhizal structures in the root as extramatrical mycelium in the first stages of the plant. Spores of the germinated species were seen and formed an internal germination and colonisation network. The values of colonisation depending on the times of corn growth are also shown.

Example 7. Results Obtained in the Field with the Application of the Composition of the Invention in Micro Granulated Form in Wheat and Barley Results obtained in the field with the application of composition of the invention, comprising *Dominikia* sp. deposited under accession number MUCL 57072, in micro-granulated form in wheat and barley are reported in following Table 11.

TABLE 11

| Crop | Variety | Irrigation | Treated (kg · ha$^{-1}$) | Not Treated (kg · ha$^{-1}$) | Improvement (%) |
|---|---|---|---|---|---|
| Barley | Voley | Rainfed Cultivation | 2600 | 3000 | 15 |
| Barley | Signoro | Irrigated Cultivation | 7100 | 7700 | 8.5 |
| Wheat | Bonifacio | Irrigated Cultivation | 6350 | 7000 | 10.2 |
| Wheat | Badrá | Irrigated Cultivation | 4981 | 5463 | 9.7 |
| Wheat | Chambo | Rainfed Cultivation | 3350 | 3700 | 10.4 |
| Wheat | durum | Rainfed Cultivation | 4300 | 4900 | 14 |
| Wheat | durum | Rainfed Cultivation | 4570 | 5110 | 11.8 |
| Wheat | durum | Irrigated Cultivation | 6345 | 7135 | 12 |

Example 8. Results Obtained in the Field with the Application of the Composition of the Invention in Micro Granulated Form in Corn Results obtained in the field with the application of the composition of the invention, comprising *Dominikia* sp. deposited under accession number MUCL 57072, in micro-granulated form in corn are reported in following table 12.

TABLE 12

| | Variety-Cycle | Irrigation | Not Treated (dry Matter) | Treated (dry Matter) | IMPROVEMENT (kg/ha) |
|---|---|---|---|---|---|
| Zone 1 | Lg 30369-365 | Irrigated | 7.87 | 8.25 | 809.091 |
| Zone 2 | Lg 30369-365 | Irrigated | 4.24 | 5.27 | 2408.655 |
| Zone 3 | Lg 30369-335 | Irrigated | 4.85 | 5.26 | 963.080 |
| Zone 4 | Lg 30369-365 | Irrigated | 6.84 | 7.89 | 2085.287 |
| Zone 5 | Maisadour-350 | Irrigated | 7.40 | 8.09 | 1379.649 |

Example 9. Micorrhizal Activity of *Dominikia* sp. in the Cultivation of Rice (*Oriza Sativa*) in Flooded Soil An experiment was carried out to define the mycorrhizal activity of the composition of the invention containing *Dominikia* sp., deposited under accession number MUCL 57072, in concentrated form, in flooded saline soil conditions. The composition used had a concentration between $1-4 \times 10^6$ propagules/g of substrate. Conversely, according to embodiments, the concentration of the composition may be between $1-2 \times 10^4$, preferably between $1,2-1, 8 \times 10^4$ propagules/g of substrate.

Materials and Methods:

The experiment was performed at the "Tres Caminos" experimental farm owned by CEBAS-CSIC and located in the Matanza area, municipality of Santomera (Murcia). The plants were grown in a monolayer tunnel-type experimental greenhouse with an approximate surface area of 60 m2, covered with polycarbonate and top window protected with antitrips mesh. It was equipped with a cooling system and an aluminised screen shade system. The trial was performed with rice plants (*Oriza sativa*), variety J 104, subjected to two mycorrhizal inoculant treatments and the corresponding control without mycorrizal treatment. The mycorrizal treatment was the composition of the invention containing *Dominikia* sp., deposited under accession number MUCL 57072, in concentrated form at a dose of 1 kg/ha coating the rice seed.

When the inoculation was assured in individual shoots, at 15 days after germination, the plants were transplanted at a concentration of 10 plants per concrete channel, of 2 m2 surface area, using Hidromórfico Gley Nodular Salinizado soil, according to the UNESCO soil classification (Hernádez, A; Perez, J. M; Bosch, D; Rivero, L: Nueva Version de Clasificación Genetica de los Suelos de Cuba. Soil Institute. AGRINFOR, La Habana, 1999. 64p) as a substrate in both containers. The main features are shown in Table 1. The cultivation work was performed and a layer of water was added after 18 days of sowing the seeds in all treatments.

TABLE 13

Some chemical properties and number of spores. 50 g soil$^{-1}$ of Hidromórfico Gley Nodular Salinizado soil used in the experiment.

| M.O (%) | pH | P (cmol · kg$^{-1}$) | Ca | Mg | K | Na | C.E (µS · cm$^{-1}$) | No spores · g soil$^{-1}$ |
|---|---|---|---|---|---|---|---|---|
| | | | cmol · kg$^{-1}$ | | | | | |
| 2.3 | 7.5 | 13.2 | 10.2 | 5.6 | 0.9 | 2.2 | 2876 | 1.2 |

Characteristics of the Composition of the Invention in Concentrated Form

In the present example, the mycorrhizal inoculant composition of the invention in concentrated form, contains the arbuscular mycorrhizal forming fungus *Dominikia* sp. deposited under accession number MUCL 57072. The composition used had a concentration between $1\text{-}4\times10^6$ propagules/g of substrate.

Determinations Performed

The dynamics of growth for 90 days post transplanting (dpt) was determined, where the plant height and depth of the root system was measured and also the harvest yield and some of its components.

Mycorrhizal action was determined during crop development by performing measurements of percentage colonisation (%), visual density (%), arbuscular extramatrical mycelium and arbuscular endophytes using a stereo microscope (Zeiss, West Germany -5-) and an Axiostar compound microscope (Zeiss, West Germany). The ratio between arbuscular external and endophyte mycelium was calculated (MEA:EA).

Mycorrhizal evaluation of the samples was performed using the root staining technique (Phillips, D. M and Hayman, D. S. Improved procedures for clearing roots and staining parasitic and vesicular arbuscular mycorrhizal fungi for rapid assessment of infection. Trans. Br. Mycol. Soc. 55. 158-161. 1970) and the percentage colonisation was determined by the method of intercepts (Giovannetti, M. and Mosse, B. (1980): An evaluation of techniques to measure vesicular-arbuscular infection in roots. New Phytology., 84:489-500). The mathematical calculation of visual density, arbuscular endophytes and mycorrhizal activity was determined according to proposed protocols (Trouvelot, A., Kough, J. and Gianinazzi Pearson, V. (1986). Mesure du Taux de Mycorhization VA d'un Systeme Radiculaire. Recherche de Methodes d'Estimation ayant une Signification Fonctionnelle. Proceedings of the 1st European Symposium on Mycorrhizae: Physiological and Genetical Aspects of Mycorrhizae, Dijón, 15 Jul. 1985. (eds. V. Gianinazzi Pearson and S. Gianinazzi). INRA, Paris. pp. 217 222; Herrera-Peraza, R. Eduardo Furrazola, Roberto L. Ferrer, Rigel Fernandez Valle and Yamir Torres Arias. 2004. Functional strategies of root hairs and arbuscular mycorrhizae in an evergreen tropical forest, Sierra del Rosario, Cuba. Revista CENIC Ciencias Biologicas, Vol. 35, No. 2, 2004). The total spore populations. g soil$^{-1}$ were also determined.

Statistical Analysis

The statistical processing of the results were performed by simple analysis of variance of classification and Tukey's test was used when there were significant differences between means, using the program Statgraphics® Plus, 4.1. For drawing graphs (i.e., FIGS. 1, 2 and 3), the SigmaPlot 4 program was used.

The percentage values of mycorrhizal colonisation were transformed using the expression 2aresen√x.

Results and Discussion

Table 13, above reported, shows some of the chemical properties of the soil used in the experiment. The soil had a slightly alkaline pH, average levels of organic matter, P and values of $Ca^{2+}$ of the order of 10 cmol·kg$^{-1}$. Regarding the saline characteristics, there were high contents of Na and high electrical conductivity, indicating strongly saline characteristics, although fertility was acceptable for development of a rice crop.

The number of spores found in this substrate was very low, a feature of heavily used agricultural soils where the diversity and intensity of arbuscular mycorrhizal fungi (AMF) is reduced, given intensive tillage, overexploitation and typical chemicalization and salinization processes, etc. (Rao, D. L. N., 1998. Biological amelioration of salt-affected soils. In: Microbial Interactions in Agriculture and Forestry, vol. 1. Science Publishers, Enfield, USA, pp. 21-238)

The analysis of the growth dynamics of rice plants under these conditions showed distinct behaviour with the treatments in the variables studied. The height of the plants increased steadily, accelerating their growth after day 27 (Table 14).

TABLE 14

Height (cm), depth of root system (cm) and mycorrhizal colonisation (% MC) in plants treated with *Dominikia* sp. (D.t) and control (C) plants during 90 dpt in saline soil conditions.

| DPT | 1 | 7 | 10 | 13 | 18 | 20 | 23 | 27 | 32 | 39 | 60 | 90 |
|---|---|---|---|---|---|---|---|---|---|---|---|---|
| Height | | | | | | | | | | | | |
| D.t | 10.5 b | 10.5 b | 10.9 b | 12.4 b | 13.0 b | 17.1 a | 17.0 a | 19.8 | 23.8 a | 32.8 a | 63.5 a | 74.1 a |
| C | 11.1 a | 11.2 a | 12.2 a | 14.4 a | 15.6 a | 15.6 b | 16.7 b | 18.9 | 20.7 b | 25.7 b | 58.6 b | 68.1 b |
| St. Sig. | 0.2*** | 0.12*** | 0.1*** | 0.2*** | 0.3*** | 0.2*** | 0.4*** | 0.9 ns | 0.1*** | 0.2*** | 0.6*** | 0.2*** |
| DRS | | | | | | | | | | | | |
| D.t | 0 | 0.6 | 1.4 b | 2.6 | 4.3 | 6.18 | 6.48 | 6.82 | 7.9 a | 7.08 | 13.9 a | 16.9 a |
| C | 0 | 0.6 | 2.1 a | 2.1 | 4.7 | 6.29 | 6.32 | 6.4 | 6.4 b | 7.23 | 10.4 b | 13.1 b |
| St. Sig. | 0.0 ns | 0.3 ns | 0.2*** | 0.6 n.s | 0.8 ns | 0.3 ns | 0.5 ns | 0.4 ns | 0.2*** | 0.3 ns | 0.1*** | 0.2*** |
| (% MC) | | | | | | | | | | | | |
| D.t | 2 a | 6 a | 13 a | 14 a | 14 a | 17 a | 18 a | 24 a | 35 a | 38 a | 38 a | 41 a |
| C | 0 b | 3 b | 3 b | 6 b | 10 b | 12 b | 13 b | 15 b | 20 b | 21 b | 19 b | 22 b |
| St. Sig. | 0.3*** | 0.2** | 0.13*** | 0.4*** | 0.6*** | 0.1*** | 0.2*** | 0.1*** | 0.2*** | 0.3*** | 0.2*** | 0.4*** |

Legend: DRS: Depth of root system, DPT: Days post treatment, St. Sig.: Standard Deviation.

Same letters in the same column do not differ significantly at p 0.05.

Both treatments show significant differences during height gain. The highest values were obtained in the control treatment up to 18 days, after which there was a change in behaviour and highest values for plant height were obtained in the inoculant treatment with the efficient arbuscular mycorrhizal fungus.

The analysis of the growth dynamics of rice plants under these conditions revealed distinct behaviour of the variables with the treatment. The height of the plants increased steadily, accelerating their growth after day 27.

Both treatments show significant differences during height gain. The highest values were obtained in the control treatment up to 18 days, after which there was a change in behaviour and highest values for plant height were obtained in the inoculation treatment with the efficient arbuscular mycorrhizal fungus.

A similar behaviour of the height variable was observed in the root system depth, which was greater in treated than control plants after 32 dpt. In this case, the behaviour was accentuated because this is the part of the plant where the fungus is established.

The study of mycorrhizal colonisation showed distinct behaviour to that found in the previously analysed variables. In this case and in both treatments, colonisation was progressive and always reached highest values in the inoculated treatment compared to the control treatment, which although was not inoculated showed natural levels of mycorrhizal colonisation, a typical result in experiments conducted in natural conditions.

The development was well marked in the case of treatment inoculated with AMF, reaching high values if taking into account that the experiment was conducted in flooded conditions or with a layer of water after 20 days. At the end of the cultivation, root colonisation reached a value of 44%, which is considered high compared to other studies of mycorrhizae in rice, where the colonisation maximums do not exceed 25% with inoculation on a solid base. (Fernández, F.; Ortiz, R.; Martinez, M. A.; Costales, A.; Llonín, D. The effect of commercial arbuscular mycorrhizal fungi (AMF) inoculants on rice (Oryza sativa) in different types of soils. Cultivos Tropicales 18 (1): 5-9, 1997).

Figure 2:
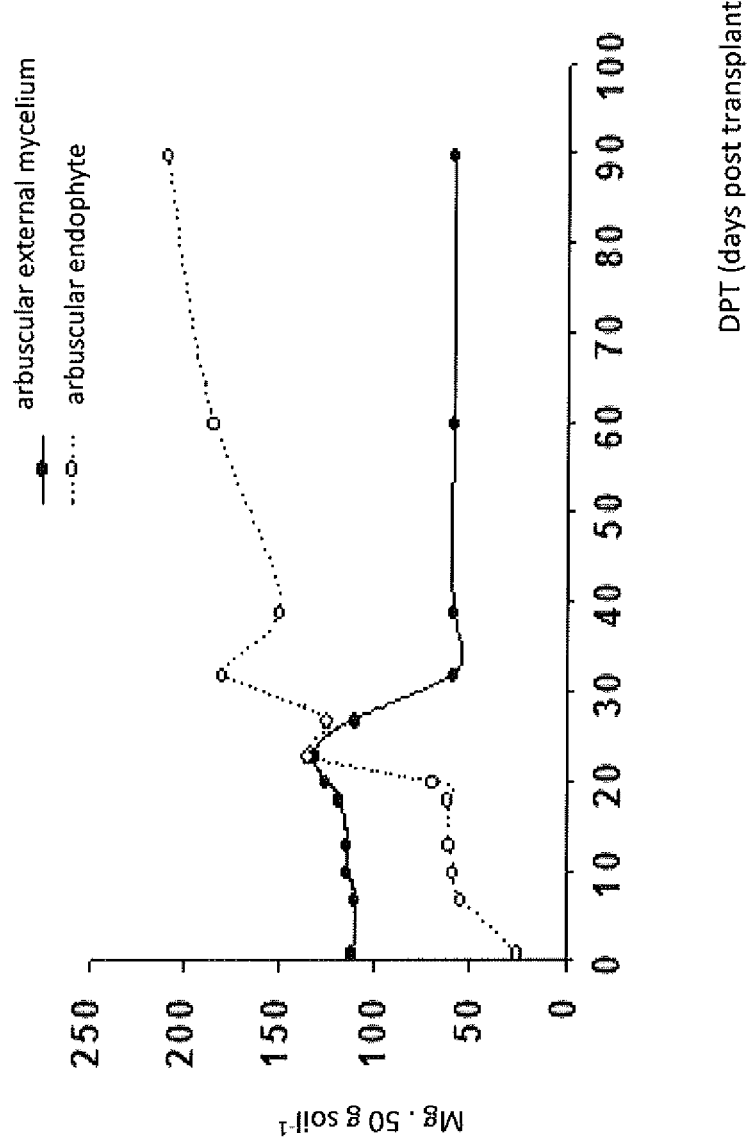
FIG. 2: Behaviour of the arbuscular external mycelium and the arbuscular endophyte in the treatment with *Dominikia* sp.

FIG. 1 shows the development of two very important fungal variables in mycorrizal activity in the treatment with the inoculant with the composition of the invention in concentrated form, the population of spores and fungal occupation, expressed through the visual density percentage, which is nothing other than the intensity with which the mycelium colonises the interior root.

The visual density showed a typical microbial behaviour with a well-defined latency phase where the fungus slowly colonised the root interior from 0 to 20 days and subsequently showed exponential growth to 40 days, the time when it reached the stationary phase and the end of the cultivation.

In the case of the spore population, values in the soil were detected in the first days, derived from the inoculation (up to 15 days in the stems), which then gradually disappeared over time, product of the germination in favourable conditions of humidity and high temperature until their population in the soil fell. After 30 days, production of new spores started, derived from the development of external fungal biomass and development of symbiosis with the plant. In this case, the population continued to grow to values close to 12 spores. $g^{-1}$ de soil.

The analysis of the arbuscular external mycelium and the arbuscular endophytes variables (FIG. 2) is very interesting as it shows how the internal and external behaviours of the mycorrhizal symbiont occur as symbiosis develops in annual cultivation cycles.

In this case high values of external mycelium were observed during the first stages of symbiosis development, caused by the fungal growth at the expense of that of the plant, expressed after some years (Bethlenfalvay, G. J., Brown, M. S., Franson, R. L., Mihara, K. L., 1989. The glycine-*glomus*-bradyrhizobium symbiosis. IX. Nutritional, morphological and physiological response of nodulated soybean to geographic isolates of the mycorrhizal fungus of *Glomus mosseae*. Physiol. Plant. 76, 226-232), as a frank parasitic process, derived from exuberant growth of the mycelium in early stages of mycorrhizal colonisation in plants (hours) with a low photosynthetic phase and a high metabolic cost. The development of arbuscular endophytes follows the opposite tendency. There were very low values during the first few days, not achieving significant growth until after 25 days of growth, a stage considered to be transitional in arbuscular mycorrhizal symbiosis.

After 30 days there is a reduction and stabilisation of the external mycelium and a gradual increase of the endophyte related to plant growth and development of symbiosis.

Figure 3:
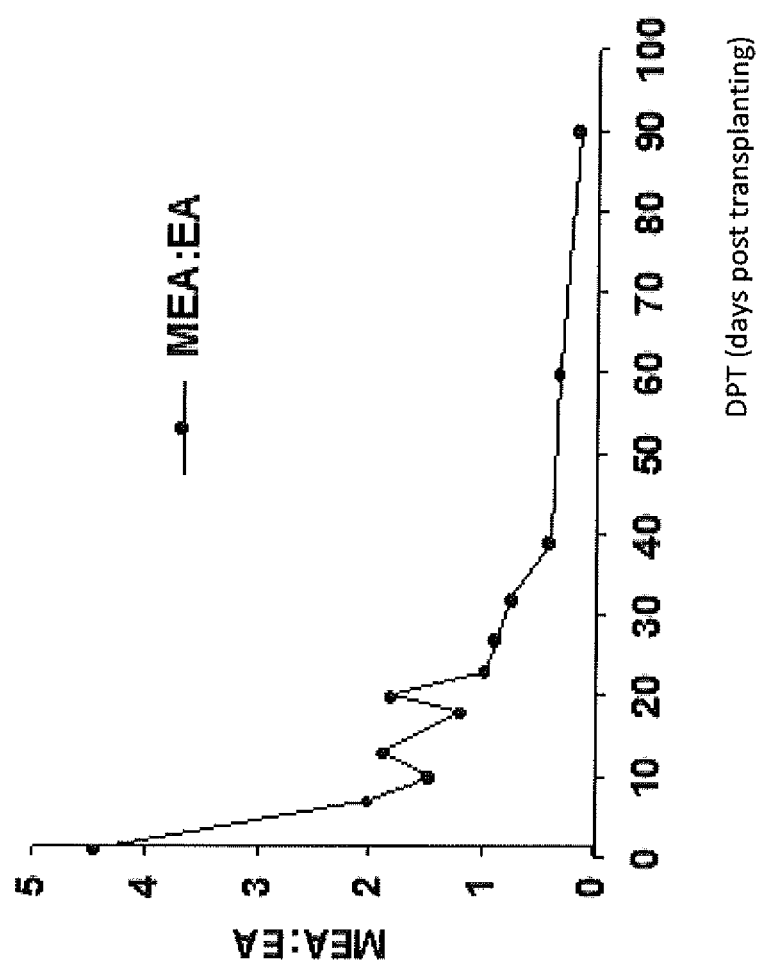
FIG. 3: Relationship between the external arbuscular mycelium and the arbuscular endophyte in the treatment with the *Dominikia* sp.

FIG. 3 shows the relationship established between the mycorrhizal components in the rice crop (The ratio between arbuscular external mycelium and endophyte mycelium (MEA:EA)). This correspondence between the two main components of symbiosis, the external mycelium and the endophyte, expresses the activity of this association, which passes through different stages of development. (Hirrel, M. C., 1981. The effect of sodium and chloride salts on the germination of Gigaspora margaria. Mycology 43, 610-617).

An initial stage where there are high values of external mycelium in correspondence with very low values of endophytes, which propitiates a frank parasitism, expressed not only by these variables but also in a reduction of plant growth compared to the non-inoculated or inefficiently mycorrhized control, which does not cause substantial changes in plant development (Table 2).

An intermediate or transition phase where both parts start to balance and a mutualist phase of exchange, when the components equilibrate with a value of 1 and even less, so that there is a notable increase inside the root that ensures proper exchange of nutrients at the level of the arbuscules inside the cells.

For this crop in particular, two phases can be well defined; an initial-transition, up to 20-25 days and a mutualist phase after this time. Parallel to this, an analysis of plant height shows a take-off in plant growth in relation to the non-inoculated control after 27 days of planting, which coincides with the mutualist phase of the mycorrhizal symbiosis under these salinity conditions.

This effect can be subsequently shown in the analysis of the yield and of its components (Table 15).

TABLE 15

Number of panicles per plant (n), weight of panicles (g), weight of 100 grains (g) and yield (g. plant$^{-1}$) in rice plants treated with *Dominikia* sp. (D.t) and control untreated plants (C) in saline soil.

| Treatments | NPP | PP | P 100 g | R |
|---|---|---|---|---|
| D.t | 8.33 a | 2.70 a | 3.69 a | 21.66 a |
| C | 5.40 b | 1.87 b | 2.70 b | 15.40 b |
| St. Sig. | 0.12 *** | 0.05 *** | 0.001 *** | 1.34 *** |
| C.V (%) | 11.2 | 9.2 | 6.5 | 14.6 |

Legend: NPP: number of panicles per plant (n), PP: Weight of panicles (g), P100 G: Weight of 100 grains (g), R: yield (g.plant$^{-1}$), St. Sig.: StandardDeviation. Same letters in the same column are not significantly different at p ≤ 0.05.

There was an increase in all the components of the yield measured in plants treated with *Dominikia* sp. compared to control non-inoculated plants. This was particularly interesting in the salinity conditions of the work.

By way of conclusion, the use of this strain of mycorrhizal fungus was effective for these soil conditions. This is very interesting as a viable and sustainable alternative for the adverse conditions caused by saline stress.

The invention claimed is:

1. A *Dominikia* sp. strain comprising accession number MUCL 57072.

2. A composition comprising the *Dominikia* sp. strain, deposited under accession number MUCL 57072, wherein the concentration of the *Dominikia* sp. in the composition is from 1.0% to 4.0% by weight based on the total weight of the composition.

3. The composition according to claim 2, wherein the concentration of the *Dominikia* sp. in the composition is from 2.0% to 3.0% by weight based on the total weight of the composition.

4. The composition according to claim 2, wherein the composition is a solid composition.

5. The composition according to claim 4, wherein the composition is in the form of powder, emulsifiable concentrate, granules, or microgranules.

6. The composition according to claim 5, wherein the composition is in the form of microgranules.

7. The composition according to claim 6, wherein the microgranules have a size ranging from 500 µm to 2000 µm.

8. The composition according to claim 2, further comprising at least one pesticide selected from the group consisting of a fungicide, a bio-fungicide, an insecticide, a bio-insecticide, a nematicide and a bio-stimulant.

9. A method of using the composition according to claim 2, comprising applying the composition as a bio-stimulant to plants.

10. A method of using the composition according to claim 2, comprising applying the composition as a bio-nematicidal to plants.

11. The method according to claim 9, wherein said plants are cereals.

12. A method of using the composition according to claim 2, comprising providing the composition by coating a seed with the composition or by applying the composition in conjunction with the seeds at the time of seeding.

13. A cereal seed coated with the composition according to claim 2.

* * * * *